(12) United States Patent
Olejniczak et al.

(10) Patent No.: US 6,740,033 B1
(45) Date of Patent: May 25, 2004

(54) MULTI-PARAMETER CAPABILITY TRANSMITTER FOR WIRELESS TELEMETRY SYSTEMS

(75) Inventors: Stefan Olejniczak, Stuttgart (DE); Andres Boos, Bondorf (DE); Werner Jacoby, Nufringen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 324 days.

(21) Appl. No.: 09/594,148

(22) Filed: Jun. 15, 2000

(30) Foreign Application Priority Data

Jun. 18, 1999 (EP) .............................. 99111750
Feb. 15, 2000 (EP) .......................... 00103015

(51) Int. Cl.[7] .............................. A61B 5/00
(52) U.S. Cl. ............... 600/301; 128/903; 340/870.16; 600/300
(58) Field of Search ............... 128/903, 904; 600/300, 301, 323, 338, 485, 486, 509, 511, 529, 588, 591, 546, 549; 340/825.36, 825.4, 870.16, 573.1

(56) References Cited

U.S. PATENT DOCUMENTS 5,373,852 A * 12/1994 Harrison et al. ............ 128/903
5,416,695 A    5/1995 Stutman et al.
5,511,553 A * 4/1996 Segalowitz ................. 128/903
5,855,550 A    1/1999 Lai et al.
5,938,619 A * 8/1999 Dogre Cuevas ............ 600/549
6,398,727 B1 * 6/2002 Bui et al. ................... 600/300

FOREIGN PATENT DOCUMENTS

WO          WO 9403105         2/1994

* cited by examiner

Primary Examiner—Eric F. Winakur
Assistant Examiner—David J. McCrosky

(57) ABSTRACT

A transmitter 110 physically comprises a (local) sensor 120, normally located within a transmitter casing 130, for sensing a first parameter, a data transmission unit 140 for providing a wireless transmission to a receiver 150 of the telemetry system 100, and a coupling unit 170 for coupling one or more remote sensors 200$i$ to the transmitter. While the transmitter is designed to transmit signals from the local sensor, it also allows to further or alternatively transmit signals from one or more remote sensors coupled to the coupling unit. This allows changing monitoring from one parameter to another parameter by simply coupling another remote sensor to the coupling unit.

19 Claims, 2 Drawing Sheets

United States Patent US 6,740,033 B1

MULTI-PARAMETER CAPABILITY TRANSMITTER FOR WIRELESS TELEMETRY SYSTEMS

BACKGROUND OF THE INVENTION

The present invention relates to wireless telemetry systems in general and, more particularly, for medical purposes.

Wireless telemetry is generally defined as a (more or less automated) communication process by which measurements are made and/or other data collected at remote or inaccessible points, and transmitted (using wireless radio transmission) to a receiving equipment for monitoring, display, and/or recording. In particular medical applications increasingly apply wireless telemetry systems, e.g. for pulse oximetry or electrocardiography. The term telemetry as used hereinafter shall apply to wireless telemetry systems only.

Telemetry systems normally comprise a transmitter for transmitting electromagnetic signals, e.g. from a measurement, and a receiver for receiving the electromagnetic signals from the transmitter. In current medical telemetry systems, the transmitter is usually carried by the patient and the receiver is typically installed in an operator room. Large systems may have a multitude of transmitters and receivers. Each transmitter normally operates with a corresponding receiver on a certain channel, preferably over a pre-defined carrier frequency.

In medical applications, in particular, it is often required to simultaneously monitor a plurality of different parameters, such as heart rate or oxygen saturation, each requiring a specific measuring setup. Telemetry systems, on the other hand, are intentionally applied, in some applications, in order to improve a patient's comfort, freedom and privacy or to be used for monitoring during transportation. Thus, it is desired to reduce the number and volume of devices directly or indirectly attached to the patient.

The most common telemetry systems in medical applications are single-parameter telemetry systems, whereby a complete telemetry system comprising sensor and transmitter is required for each parameter to be monitored. Consequently, hospitals need a plurality of different transmitters for each parameter, thus requiring a high demand of logistics, and, more seriously, a different transmitter has to be applied to the patient for changing monitoring from one parameter to another.

The Agilent Viridia 50 T (M1310A) Fetal Telemetry System of Agilent Technologies addresses the contravening objectives of, on one hand, monitoring a plurality of parameters and, on the other hand, reducing the number of required telemetry components. The system allows monitoring the parameter fetal heart rate (FHR) via ultrasound or direct electrocardiogram (ECG), and the parameter uterine activity via an external Toco transducer or an internal intrauterine pressure (IUP) transducer. As depicted in FIG. 1, up to two transducers 10 and 20 can be connected to a small lightweight transmitter 30 that is worn by the patient. Signals representing the parameters fetal heart rate, uterine activity and fetal movement profile (FMP) are transmitted continuously via radio frequency from the transmitter 30 to a (not shown) telemetry receiver, where the signals are displayed and recorded on a monitor.

Another constraint in medical applications is that the spacing (typically 25 kHz) and bandwidth of radio frequency (RF) channels in bands is usually fixed due to telecommunication regulations. While the limited bandwidth limits the amount of data that can be transmitted, even a low bandwidth parameter has to use a full bandwidth RF channel thus wasting limited RF spectrum.

The aforementioned Agilent Viridia 50 T Fetal Telemetry System allows to simultaneously transmit the (higher bandwidth) parameter of fetal heart rate (FHR) and the (lower bandwidth) parameter of uterine activity within one RF channel and via one RF transmitter. This addresses both, the limited RF bandwidth problem and also logistics problems since the number of components and different transmitters is reduced.

Another solution to overcome the limited RF bandwidth, as applied e.g. in the Agilent M2601A series also of Agilent Technologies, is to add selection means to an ECG transmitter for selecting one ECG wave out of many leads connected to the patient, and transmitting only the selected wave. A further solution, also applied e.g. in the Agilent M2601A series, is to transmit two ECG waves (higher bandwidth parameters) together with an SpO2 (lower bandwidth parameter) signal.

SUMMARY OF THE INVENTION

Although the solutions as discussed above already provide a significant improvement over single-parameter telemetry systems, it is still an object of the present invention to reduce the amount of required monitoring logistics and to further improve the patient's comfort, freedom and privacy by decreasing the number and volume of devices directly or indirectly attached to the patient.

The invention solves this object by providing transmitters, according to the independent claims, in wireless telemetry systems, preferably for medical purposes, thus providing open multi-parameter telemetry systems. Preferred embodiments are shown by the dependent claims.

As a first aspect, a transmitter physically comprises a (local) sensor, normally located within a transmitter casing, for sensing a first parameter, a data transmission unit for providing a wireless transmission to a receiver of the telemetry system, and a coupling unit for coupling one or more remote sensors to the transmitter. While the transmitter is designed to transmit signals from the local sensor, it also allows to further or alternatively transmit signals from one or more remote sensors coupled to the coupling unit. This allows changing monitoring from one parameter to another parameter by simply coupling another remote sensor to the coupling unit. Accordingly, a further parameter might be monitored (within the constraints of limited transmission bandwidth) by coupling a further remote sensor to the coupling unit. Thus, for changing the parameter(s) to monitor, the transmitter already applied to the patient needs not to be changed or removed from the patient. Simply, another remote sensor is coupled to the coupling unit.

In a preferred embodiment, the transmitter further comprises a selecting unit for selecting data supplied from the local and/or the remote sensor(s) to be transmitted by the transmitter. The selecting unit allows to manually and/or automatically select the data to be transmitted, e.g. in accordance with bandwidth or other transmission path constraints. Possible criteria for selecting data to be transmitted can be physiological data (e.g. "select the physiologically most meaningful sensor, when more than one sensor provide data about the same parameter(s)"), mechanical information (e.g. by a plugged sensor detection), electrical information (e.g. electrode impedance detection), alarm condition(s) (e.g. "transmit parameter A after a certain alarm has occurred"), and/or status condition(s) (e.g. "transmit parameter A only when a certain condition of the patient has been detected").

As a second aspect, a transmitter comprises a data transmission unit for providing a wireless transmission to a receiver of the telemetry system, and a coupling unit for coupling one or more sensors to the transmitter. The coupling unit provides an interface allowing any sensor to couple to the transmitter via a predefined protocol.

Thus, the invention provides the following advantages:

Optimum use of limited Radio Frequency spectrum by transmitting multiple parameters within one single RF channel.

Easy logistics. The hospital needs only a few different transmitters (or wireless transducers), each having multiple parameter capability.

Selection of optimum parameter is possible at patient side without changing transducers.

It is clear that the invention can be partly or entirely embodied by one or more suitable software programs, which can be stored on or otherwise provided by any kind of data carrier, and which might be executed in or by any suitable data processing unit.

BRIEF DESCRIPTION OF THE DRAWINGS

Other objects and many of the attendant advantages of the present invention will be readily appreciated and become better understood by reference to the following detailed description when considering in connection with the accompanied drawings. Features that are or can be built up substantially equally or similarly are referred to with the same reference sign.

DETAILED DESCRIPTION OF THE INVENTION

Figure 1:
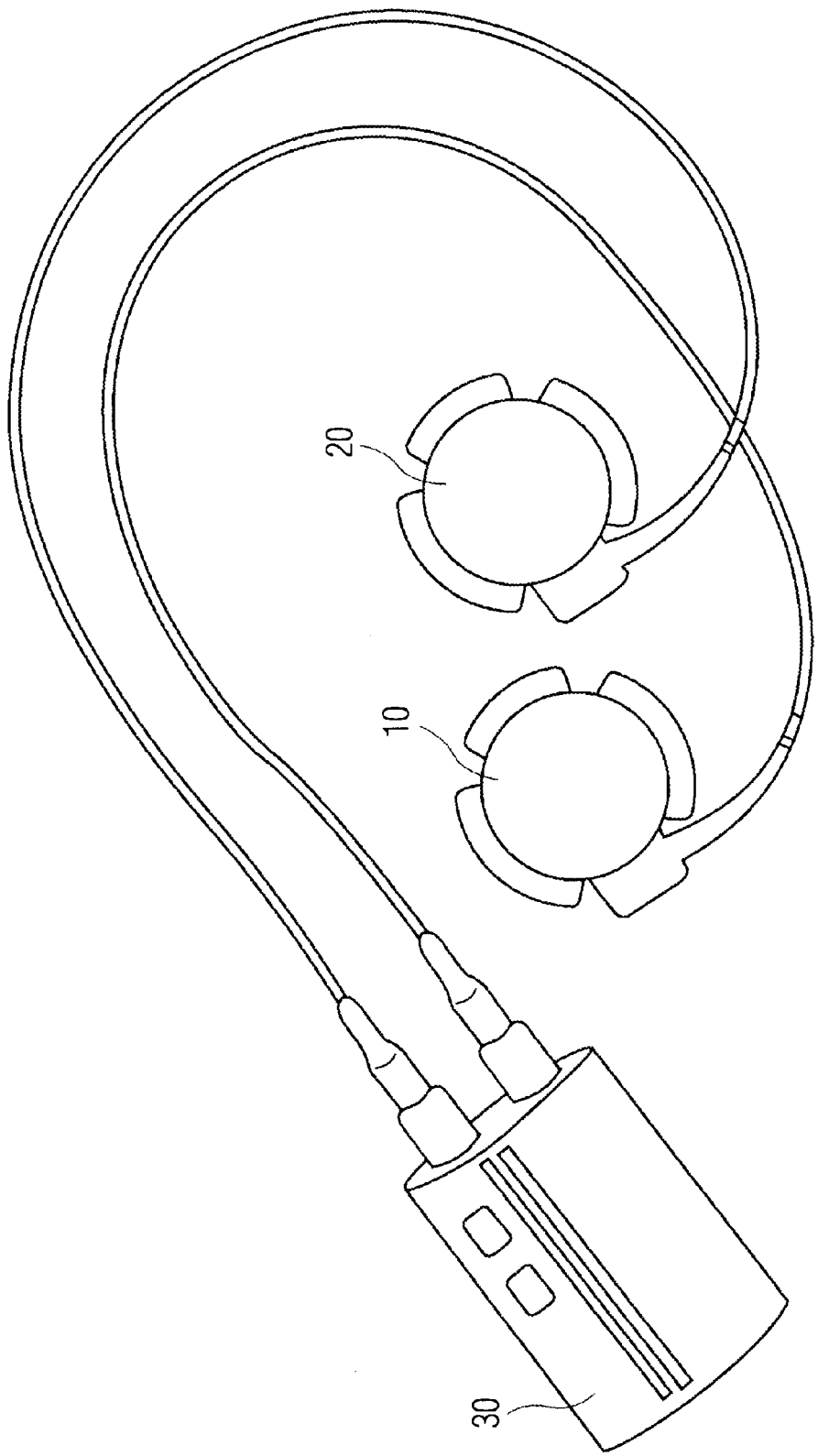
FIG. 1 shows a wireless telemetry system of the art.
Figure 2:
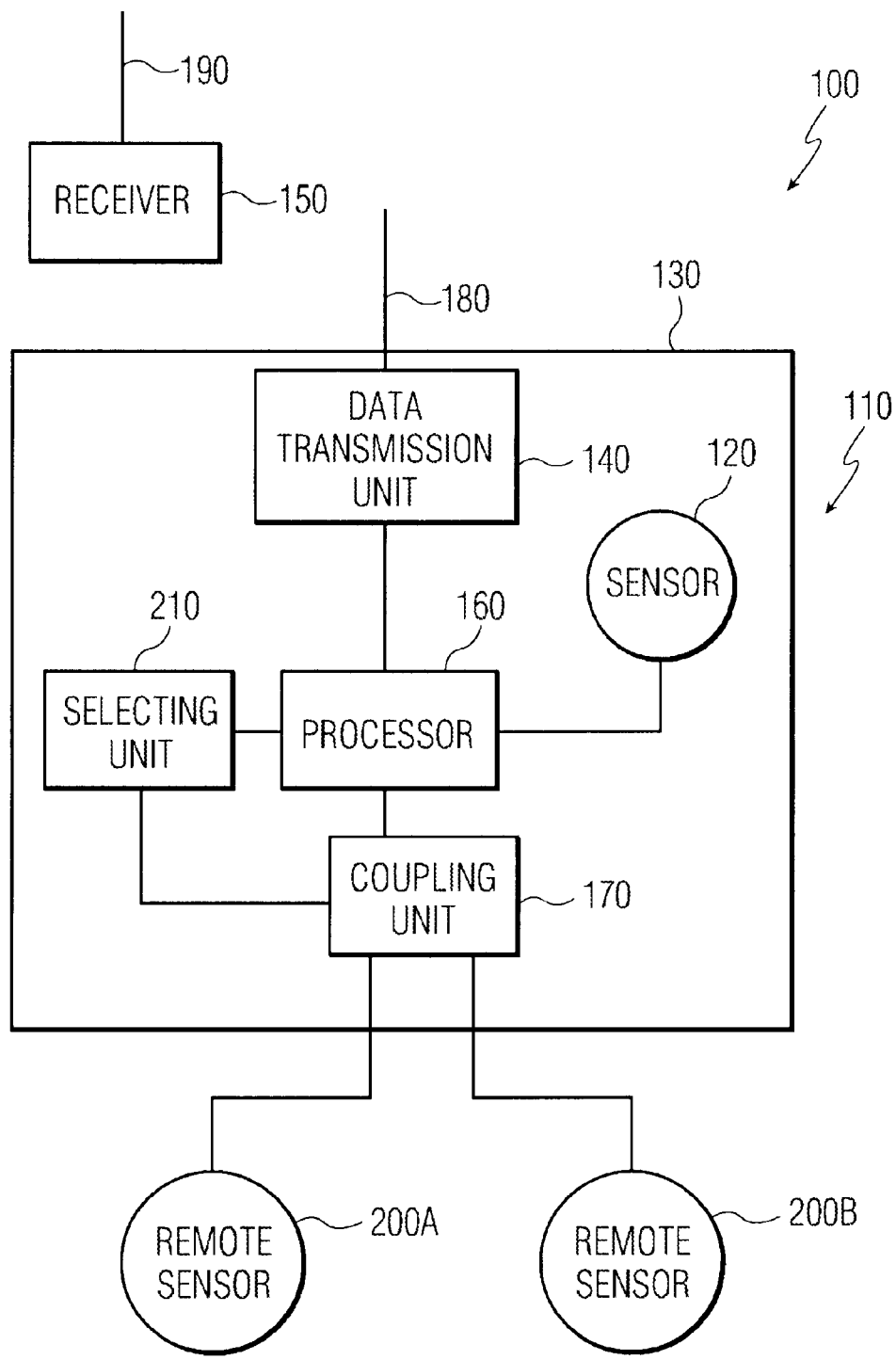
FIG. 2 shows a telemetry system 100 according to the invention.

FIG. 2 shows a telemetry system 100 according to the invention. A transmitter 110 physically comprises a (local) sensor 120, normally located within a transmitter casing 130, for sensing a first parameter, a data transmission unit 140 for providing a wireless transmission to a "(generally distant)" receiver 150 of the telemetry system 100, a processing unit 160, and a coupling unit 170. For the sake of simplicity, the term 'parameter', as used herein, shall also represent the measured/sensed signals of that parameter.

In a stand-alone operation mode of the transmitter 110, the sensor 120 senses the first parameter, and provides the sensed signals to the processing unit 160 for processing the sensed signals. For transmitting the sensed signals to the receiver 150, the data transmission unit 140 receives the signals to be transmitted from the processing unit 160 and transmits those signals, e.g. via an antenna 180 of the transmitter 110 to (e.g. an antenna 190 of) the receiver 150. This kind of parameter sensing and wireless transmission is well known in the art needs not be explained in detail herein.

The processing unit 160 may contain a digital signal processor (DSP) and/or an analog signal processing (comprising e.g. filters, amplifiers, mixers, etc.), for extracting parameters from the sensor signals, in order to control the selecting unit 210.

While the transmitter 110 is designed to transmit signals from the local sensor 120, it also allows to further or alternatively transmit signals from one or more remote sensors 200i (with i=A, B, C, . . . ) coupled to the coupling unit 170. This allows changing monitoring from one parameter to another parameter or between different sensors monitoring the same parameter by simply coupling another remote sensor 200i to the coupling unit 170. In the following for the sake of simplicity, the term "changing monitoring from one parameter to another parameter", or corresponding terms, shall also cover the meaning "changing between different sensors monitoring the same parameter".

Accordingly, a further parameter might be monitored (within the constraints of limited transmission bandwidth) by coupling a further remote sensor 200i to the coupling unit 170. Thus, for changing the parameter(s) to monitor, the transmitter 110 already applied to the patient needs not to be changed or removed from the patient. Simply, another remote sensor 200i needs to be coupled to the coupling unit 170.

The coupling unit 170 may comprise a mechanical part (e.g. a connector or a 'snap on fix' connection) in order to mechanically fix the remote sensor(s) 200i. It may also contain parts (e.g. electrical wires, infrared sensors, and/or inductive coils) in order to provide a communication with the remote sensor(s) 200i. The hardware can be implemented with a serial or parallel port, e.g. as known from Personal Computers, or with an optical infrared link, as shown e.g. from Palmtop Computers, or with other communication links as well known in the art.

The remote sensors 200i are preferably coupled to the coupling unit 170 by means of wired connections as well known in the art. However, other connection types such as infrared or inductive coupling are also applicable accordingly.

It is to be understood that while in some applications not all of the sensed signals or parameters shall be transmitted to the receiver 150, in other applications a concurrent transmission of all sensed parameters is either not wanted or simply impossible. Typical applications of the former cases are that when the same parameter is sensed by different sensors (e.g. using different sensing technologies/types or different application sites), like fetal heart rate by Fetal Ultrasound and Fetal ECG. Typical applications of the latter case are due to technical constraints such as limited bandwidths. In either case, a selection of one or more of the parameters or signals from the sensor(s) 200i as well as of the sensor 120 might be required. For that purpose, the transmitter 110 of a preferred embodiment further comprises a selecting unit 210, which is preferably part of the processing unit 160.

The selecting unit 210 allows selecting data supplied from the local sensor 120 and/or the remote sensor(s) 200i coupled to the coupling unit 170. The selecting unit 210 allows to manually and/or automatically select the data to be transmitted, e.g. in accordance with bandwidth or other transmission path constraints. Possible criteria for selecting data to be transmitted can be:

(a) physiological data (e.g. "select the physiologically most meaningful sensor, when more than one sensor provides data about the same parameter(s)"), (b) mechanical information (e.g. by a plugged sensor detection), (c) electrical information (e.g. electrode impedance detection), (d) alarm condition(s) (e.g. "transmit parameter A after a certain alarm has occurred"), and/or (e) status condition(s) (e.g. "transmit parameter A only when a certain condition of the patient has been detected").

In case of (a) selection by means of physiological data, the selecting unit 210 evaluates the applied signals (from the local sensor 120 and/or the remote sensor(s) 200i coupled to the coupling unit 170) according to predefined criteria such as noise level (e.g.: select the sensor which gives the smallest heart rate jitter), expected physiological range (e.g.: reject sensors which obviously provide wrong data). This might already represent a preprocessing of the measured signals.

In case of selection by means of (b) mechanical information and/or (c) electrical information, the selecting unit 210 is coupled to the coupling unit 170 e.g. for determining a type of connector or connection representing a specific type of parameter. This can be accomplished e.g. by switches, thumb wheels, keys or touchpads with or without display feedback (e.g. via soft or hard keys). The type of connector or connection can be coded mechanically (e.g. by means of shape or mechanical coding slots) or electrically (e.g. by means of impedance).

In case of selection by means of (d) alarm and/or (e) status condition(s), the selecting unit 210 selects the parameter(s) to be transmitted by the transmitter 110 based on data provided by the processing unit 160. In a preferred embodiment, the parameter with the highest alarm and/or status priority is transmitted. Therefore, the processing unit 160 may provide parameter processing, such as correlation algorithms for determining e.g. fetal heart rate from an ultrasound signal, and/or alarms processing. In case of a detected alarm on an active but not currently transmitted parameter, the selecting unit 210 switches to transmit this parameter or any information about this particular alarm condition. For example, if the processing unit 160 (e.g. with a digital signal processor) detects fetal tachycardia, transmission of maternal temperature is stopped and fetal heart rate is transmitted instead, because this has a higher physiological significance.

Manually switching between parameters can be accomplished e.g. by programming means at the receiver 150 (e.g. as a base station) or at the transmitter 110. For that purpose, the receiver 150 may therefore be provided with a graphical user interface (e.g. a PC like) or simple keys. The transmitter 110 may therefore be provided with keys and a small display.

Automatically switching between transmitted parameters is preferably provided dependent on alarm or status conditions, as explained above.

A typical application of the transmitter 110 in its stand-alone operation mode is that the transmitter 110 is attached to a patient for monitoring the parameter sensed by the local sensor 120. In case of shared-transmission operation mode of the transmitter 110, wherein one or more remote sensors 200i are coupled to the transmitter 110, a typical application will be that the transmitter 110 as well as the one or more remote sensors 200i are attached to the same patient. It is clear, however, though less practical, that the transmitter 110 can also be applied to transmit signals from different patients.

In a preferred embodiment, the coupling unit 170 provides an interface allowing any sensor to couple to the transmitter via a predefined protocol. The hardware can be implemented with a serial or parallel port, e.g. as known from Personal Computers, or with an optical infrared link, as known e.g. from Palmtop Computers, or with other communication links as well known in the art.

In a specific embodiment, the local sensor 120 is omitted in the transmitter 110, so that the transmitter 110 represents a pure transmission device without own sensing capability. However, the above said applies accordingly.

In the following, more detailed examples shall be described for an application in a telemetry system for monitoring pregnant women in the labor and delivery ward of a hospital. The following parameters are applicable for monitoring:

Higher bandwidth parameter: Fetal Ultrasound Wave, ECG Wave (fetal and maternal) SpO2 Wave (fetal and maternal), Invasive Blood Pressure Wave, Gas Wave (e.g. CO2), EEG Wave, Cardiac Output Wave, Respiration Wave.

Lower Bandwidth parameter: Fetal Heart Rate, Temperature, NIBP Values, SpO2 Values (fetal and maternal), Invasive Blood Pressure Values, Gas Values (e.g. CO2), External TOCO, Intrauterine Pressure.

The processing unit 160 allows combining multiple parameters into one RF channel applying methods as known in the art, such as:

time multiplexing (e.g. data of additional parameters can be inserted into a digital serial frame, modulating the RF carrier, until every bit of the digital serial frame is used), code multiplexing, or frequency multiplexing (e.g. in an analog system by adding one sub-carrier per additional parameter, until the maximum number of sub-carriers, limited by the pre-given RF channel bandwidth, is reached).

The measured signals for the parameters can be selected (by the selecting unit 210) and transmitted (by the data transmission unit 140) alone or in any combination, as long as the occupied (e.g. RF) bandwidth does not exceed the predefined channel bandwidth.

The following selecting methods of transmitted parameters, or any combination thereof, can be part of preferred embodiments:

Automatically switching from Fetal Ultrasound (as sensed by the local sensor 120) to Fetal ECG by connecting e.g. a Fetal ECG scalp electrode (as remote sensor 200) and sensing the impedance between the leads thereof. Measurement of the impedance between the leads can be done, e.g. by impressing a small sense current and monitoring the voltage across the leads. Once the sense current is constant, the voltage is proportional to the impedance between the leads. The selecting unit 210 switches from Fetal Ultrasound to Fetal ECG mode, if the impedance between the leads falls below a certain threshold, indicating that the fetal scalp electrode has been applied to the scalp of the fetus. This feature is especially useful for a nurse, in order to switch very fast between Fetal Ultrasound and Fetal ECG, e.g. when the fetal ultrasound signal is lost during heavy contractions of the maternal uterus during birth, thus maximizing the time of uninterrupted monitoring.

Switching from Fetal ECG (as sensed by the local sensor 120) to Fetal SpO2 (as sensed by the remote sensor 200), by connecting a Fetal SpO2 sensor and sensing its mode resistor. The mode resistor can be, for example, located within the Fetal SpO2 sensor connector. Sensing can be done with a simple impedance measurement (see above).

Switching from Maternal ECG (as sensed by the local sensor 120) to Fetal ECG (as sensed by the remote sensor 200) by connecting the respective ECG electrode and sensing the impedance between the leads, indicating which electrode is applied (see example above for sensing the impedance between the leads).

Switching from External Toco (as sensed by the local sensor 120) to Intrauterine Pressure (as sensed by the remote sensor 200) by connecting an Intrauterine Pressure sensor and sensing its mode resistor. The mode resistor can be, for example, located within the Intrauterine Pressure sensor connector. Sensing can be done with a simple impedance measurement (see above).

The following electrical and mechanical interconnections between remote sensor(s) 200 and the transmitter 110 can be part of preferred embodiments:

The transmitter 110 with a local Fetal Ultrasound sensor 120 may have an electrode connector for a remote Fetal ECG sensor 200.

Electrode connectors for Fetal ECG electrodes may be located mechanically at the Toco transducer (e.g. on the top cover). This enables the user to transmit both parameters simultaneously within one RF channel that is especially useful, because by this method the two basic fetal parameters can be measured with only one wireless transducer.

Electrode connectors for Maternal ECG electrodes may be located mechanically at the Toco transducer (e.g. on the top cover). This enables the user to transmit both parameters simultaneously within one RF channel. When used in conjunction with the fetal heart rate parameter (e.g. with a wireless Fetal Ultrasound transducer), this is especially useful, because by this method fetal and maternal heart-rate plus Toco can be measured with only two wireless transducers. Thus a cross channel heart rate verification, which checks fetal and maternal heart-rate for identity (as already used in current fetal monitors) can be done conveniently wireless.

Digital interface via a predefined protocol between remote sensor(s) 200 and the transmitter 110, especially for lower bandwidth parameters, such as NIBP, SpO2, Temperature and Gas. The selecting unit 210 senses (e.g. via a serial bi-directional protocol), which sensor 200 is connected and the transmitter 110 transmits this parameter plus status information.

What is claimed is:

1. A transmitter of a wireless telemetry system (100) for medical applications, the transmitter comprising:
   a processing unit (160);
   a data transmission unit (140) in communication with the processing unit (160), said data transmission unit being adapted for providing a wireless transmission to a receiver (150) of the telemetry system (100),
   a locally attached sensor (120) that communicates with the processing unit (160), wherein the processing unit, data transmission unit and locally attached sensor are arranged in a common housing without any wires attached to the processing unit, data transmission unit and locally attached sensor extruding from the housing; and
   a coupling unit (170) for selectively coupling one of: (1) a plurality of remote sensors (200*i*) and (2) the locally attached sensor (120) via a selecting unit (210) to the processing unit (160) based on predetermined criteria, so that a sensor signal indicative of an alert condition having a highest level of priority is coupled to the data transmission unit (140).

2. The transmitter (110) of claim 1, wherein the selecting unit (210) selects data supplied from the local sensor (120) and/or the remote sensor(s) (200*i*) to be transmitted by the data transmission unit (140).

3. The transmitter (110) of claim 2, wherein the selecting unit (210) allows to manually and/or automatically select the data to be transmitted in accordance with bandwidth or other transmission path constraints.

4. The transmitter (110) of claim 2, wherein the selecting unit (210) selects data to be transmitted according to one or more of the following criteria: physiological data, mechanical information, electrical information, alarm condition(s), and status condition(s).

5. The transmitter (110) according to claim 1, wherein the coupling unit (170) provides an interface allowing any sensor to couple to the transmitter via a predefined protocol.

6. The transmitter (110) according to claim 1, further comprising a processing unit (160) for processing sensed signals from the one or more sensors (200*i*) connected to the coupling unit (170).

7. The transmitter of claim 1, wherein the local sensor and remote sensors are attachable to a patient.

8. The transmitter of claim 1, wherein the local sensor is attachable to a first patient and the remote sensors are attachable to a different patient.

9. The transmitter of claim 1, wherein the coupling unit (170) includes an interface for coupling any additional remote sensors to the transmitter via a predetermined protocol.

10. The transmitter of claim 9, wherein the predetermined protocol is an infrared optical link.

11. The transmitter of claim 9, wherein the predetermined protocol is a radio frequency (RF) link.

12. The transmitter according to claim 1, wherein the processing unit provides the data transmission unit with data formatted in code multiplexing (CDMA) from more than one sensor.

13. The transmitter according to claim 1, wherein the processing unit provides the data transmission unit with data formatted in time multiplexing (TDMA) from more than one sensor.

14. The transmitter according to claim 1, wherein the processing unit provides the data transmission unit with data formatted in frequency multiplexing (FDMA) from more than one sensor.

15. The transmitter according to claim 1, wherein the selecting unit (210) selects data for transmission according to feedback information including mechanical information, electrical information, and physiological data.

16. A wireless telemetry system comprising:
   a locally attached sensor (120) housed within a transmitter;
   the transmitter (110) having a plurality of sensors remotely coupled thereto for selectively transmitting data from at least one of the remote sensors according to predetermined criteria so that data relating to at least one of the plurality of remote sensors that indicates an alert condition has occurred has priority in being transmitted;
   a receiver (150) located a predetermined distance from the transmitter; wherein the transmitter (110) and the receiver (150) are adapted for wireless transmission therebetween.

17. The system according to claim 16, further comprising that a first of the plurality of remote sensors is attached to a first patient and a second of the plurality of remote sensors is attached to a second patient.

18. The system according to claim 17, wherein the first and second remote sensors communicate by wireless telemetry to the transmitter, and the transmitter communicates with the receiver using one of TMDA, CMDA, and FDMA.

19. A wireless telemetry system (100) for medical applications, comprising:
   a transmitter (110) having a plurality of sensors electrically coupled thereto for selectively transmitting data from at least one of the plurality of said sensors according to predetermined criteria so that data relating to a sensor that is in an alert condition has priority in being transmitted; and
   a receiver (150),
   wherein the transmitter (110) and the receiver (150) are adapted for providing a wireless transmission therebetween, and
   wherein at least a first sensor of said plurality of sensors is a local sensor (120) arranged in a common housing (130) with the transmitter without having any wires connected to said local sensor (120) extruding from the housing.

* * * * *